(12) United States Patent
Viswanathan et al.

(10) Patent No.: US 11,183,306 B2
(45) Date of Patent: Nov. 23, 2021

(54) DUPLICATE CASE RECOMMENDATION ENGINE FOR PHARMACOVIGILANCE

(71) Applicant: Accenture Global Solutions Limited, Dublin (IE)

(72) Inventors: Praveen Viswanathan, Jodhpur (IN); Krithika Pattabiraman, Bangalore (IN); Prince Chaturvedi, Bangalore (IN)

(73) Assignee: Accenture Global Solutions Limited, Dublin (IE)

( * ) Notice: Subject to any disclaimer, the term of this patent is extended or adjusted under 35 U.S.C. 154(b) by 204 days.

(21) Appl. No.: 16/745,476

(22) Filed: Jan. 17, 2020

(65) Prior Publication Data
US 2021/0225526 A1 Jul. 22, 2021

(51) Int. Cl.
| | |
|---|---|
| *G16H 50/70* | (2018.01) |
| *G06F 16/2457* | (2019.01) |
| *G06F 16/22* | (2019.01) |
| *G16H 20/10* | (2018.01) |

(52) U.S. Cl.
CPC ......... *G16H 50/70* (2018.01); *G06F 16/2237* (2019.01); *G06F 16/24578* (2019.01); *G16H 20/10* (2018.01)

(58) Field of Classification Search
CPC .... G16H 20/10; G16H 50/30; G06F 16/2237; G06F 16/24578
USPC ....................................................... 705/2–3
See application file for complete search history.

(56) References Cited

U.S. PATENT DOCUMENTS

| | | | |
|---|---|---|---|
| 2004/0249789 A1* | 12/2004 | Kapoor | G06F 16/215 |
| 2014/0358576 A1* | 12/2014 | Hoffman | G16H 50/30 |
| | | | 705/2 |
| 2016/0048655 A1 | 2/2016 | Maitra et al. | |
| 2019/0005019 A1 | 1/2019 | Burke et al. | |
| 2019/0034475 A1* | 1/2019 | Parikh | G06N 20/20 |
| 2019/0088354 A1* | 3/2019 | Yanowitz | G06F 16/9554 |

(Continued)

OTHER PUBLICATIONS

Pham, Signal Detection Of Adverse Drug Reaction Using The Adverse Event Reporting System: Literature Review And Novel Methods, Mar. 2018, Graduate Theses And Dissertations, http://scholarcommons.usf.edu/etd/7218 (Year: 2018).*

(Continued)

*Primary Examiner* — Joy Chng
(74) *Attorney, Agent, or Firm* — Fish & Richardson P.C.

(57) ABSTRACT

Implementations of the present disclosure include receiving a document including data representative of an adverse event, providing a case including a set of fields, each field being populated with a value, querying a safety system based on a query that includes values of the case, receiving a sparse matrix based on query results responsive to the query, the sparse matrix including two or more vectors, each vector of the two or more vectors representing a historical case score, for each historical case, determining a score based on a respective vector of the two or more vectors and an input vector representative of the case, each score representing a degree of duplicity between the case and a respective historical case, and providing historical cases for display to a user, the historical cases including the two or more historical cases in rank order based on respective scores.

33 Claims, 6 Drawing Sheets

(56) References Cited

U.S. PATENT DOCUMENTS

2020/0034343 A1* 1/2020 Keskar ................ G06F 16/958

OTHER PUBLICATIONS

Noren et al., Duplicate Detection In Adverse Drug Reaction Surveillance, Jan. 2007, Data Mining And Knowledge Discovery, DOI: 10.1007/s10618-006-0052-8 (Year: 2007).*
Committee For Medicinal Products For Human Use (CHMP), 2010, Guideline On Detection And Management Of Duplicate Individual Cases And Individual Case Safety Reports, European Medicines Agency, Doc. Ref. EMA/13432/2009, pp. 1-20 (Year: 2010).*

\* cited by examiner

| Field_vector | list | 19 | [0.34, 0.34, 0.766569, 0.035236, 0.467448, 0.537988, 0.538702, 0.84972 ....] |

500

| Input_vector | list | 19 | [1, 1, 1, 1, 1, 1, 1, 1, 1, 1, ....] |

502

| Weighted_base_vector | list | 19 | [0.34, 0.34, 0.766569, 0.035236, 0.467448, 0.537988, 0.538702, 0.84972 ....] |

504

| case1 | list | 19 | [1, 1, 1, 1, 1, 1, 1, 1, 1, ....] |
|---|---|---|---|
| case2 | list | 19 | [0, 1, 0, 0, 1, 0, 1, 0, 0, 0, ....] |
| case3 | list | 19 | [1, 1, 1, 1, 1, 0, 1, 0, 0, 0, ....] |
| case4 | list | 19 | [1, 0, 1, 0, 1, 0, 1, 0, 1, 1, ....] |
| case5 | list | 19 | [1, 0, 1, 1, 1, 0, 1, 0, 0, 0, ....] |
| case6 | list | 19 | [1, 1, 1, 0, 1, 1, 1, 0, 0, 0, ....] |

506

| Case_ID | Field Level Score | Cosine Similarity | Final Score |
|---|---|---|---|
| case1 | 1 | 1 | 1 |
| case3 | 0.495975 | 0.760886 | 0.600513 |
| case2 | 0.384825 | 0.648886 | 0.483128 |
| case4 | 0.462877 | 0.725476 | 0.565163 |
| case5 | 0.532012 | 0.725476 | 0.613862 |
| case6 | 0.473724 | 0.760886 | 0.583909 |

DUPLICATE CASE RECOMMENDATION ENGINE FOR PHARMACOVIGILANCE

BACKGROUND

Adverse event reporting can be described as a process of acquisition, triage, data entering, assessment, distribution, reporting, and documenting a case. In some instances, an adverse event can be reported from multiple sources. In the field of healthcare, for example, adverse events, referred to as adverse drug reactions (ADRs), can be reported from health care professionals or patients, enterprises-driven patient support programs, clinical trials or post marketing studies, study or research by private/public institutions or individuals, and/or on digital platforms (e.g., social media). Case information captured in these sources is generally provided as free-form text.

Enterprises need to address adverse events. However, in many instances, multiple reports of the same adverse event occur. Consequently, an enterprise may require large back offices in order process large volumes of electronic documents, which can include manual review of electronic documents and extracting relevant information pertaining to an adverse event from the document. In some reporting systems, collated data is manually entered. Because information is received from multiple, disparate sources and different users using data entry programs to input data, it often occurs that duplicate reports of an adverse event are registered in reporting systems.

In order to maintain high quality data, identification of duplicate reports of an adverse event is required. In this manner, documents that are follow-ups to an adverse event that has already been reported can be managed in an appropriate manner. Traditionally, reporting systems implement manual identification of duplicate reporting using, for example, a drill-down technique. More particularly, a user (also referred to as a case processor) manually enters field combinations into a computer-implemented search tool that are used to search electronic documents, and, in response, the reporting system fires an exact match query. The user reviews the electronic documents returned in response to the query. Accordingly, traditional resources are both time- and resource-inefficient. That is, for example, repeated searching and review of electronic documents consumes computing resources (e.g., processors, memory).

SUMMARY

Implementations of the present disclosure are directed to a duplicate case recommendation engine (DCRE) to identify duplicate cases of adverse effects reported in pharmacovigilance (PV). More particularly, implementations of the present disclosure are directed to a DCRE that identifies duplicate cases present in a PV safety reporting by extracting relevant information from a potential new case, conducting a search of existing cases based on the relevant information, and providing a recommendation, if any, of one or more existing cases as potential matches to the new case based on historical data using machine-learning (ML).

In some implementations, actions include receiving, by a duplicate case recommendation engine (DCRE), a document including data representative of an adverse event, providing, by the DCRE, a case including a set of fields, each field of one or more fields in the set of fields being populated with a value, querying, by the DCRE, a safety system based on a query, the query including one or more values of the case, receiving a sparse matrix based on a set of query results provided from the safety system in response to the query, the sparse matrix including two or more vectors, each vector of the two or more vectors representing a historical case score within the safety system, for each historical case, determining, by the DCRE, a score based on a respective vector of the two or more vectors and an input vector representative of the case, each score representing a degree of duplicity between the case and a respective historical case, and providing, by the DCRE, a list of historical cases for display to a user, the list of historical cases including the two or more historical cases in rank order based on respective scores. Other implementations of this aspect include corresponding systems, apparatus, and computer programs, configured to perform the actions of the methods, encoded on computer storage devices.

These and other implementations can each optionally include one or more of the following features: each score is determined based on a field-level score and a similarity score of a respective historical case; the field-level score is determined based on the input vector and a field vector, the field vector including two or more weights, each weight associated with a respective field; each of the two or more weights is updated based on the set of query results provided from the safety system; the similarity score is calculated as a cosine similarity between the input vector and a respective vector of the two or more vectors; actions further include identifying a data value from the document, transforming the data value to provide a transformed data value, and providing the transformed value as the value populating a field in the set of fields; transforming the data value includes one of changing a format of the data value, adding data to the data value, and generating new data from the data value, the transformed value including the new data; adding data to the data value includes adding one or more of a month and a day to the data value; generating new data from the data value includes determining one of a preferred term and a high-level term from the data value, the new data including the one of the preferred term and the high-level term; actions further include receiving, by the DCRE, user input including a modification to the case to provide a modified case, querying, by the DCRE, the safety system based on a modified query, the modified query including at least one modified value of the modified case, receiving a second sparse matrix based on a second set of query results provided from the safety system in response to the modified query, and providing, by the DCRE, a second list of historical cases for display to the user, the second list of historical cases including two or more historical cases in rank order based on the second sparse matrix; and the adverse event includes an adverse drug reaction.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DESCRIPTION OF DRAWINGS

FIG. 5 depicts an example duplicate search in accordance with implementations of the present disclosure.

Like reference symbols in the various drawings indicate like elements.

DETAILED DESCRIPTION

Figure 1:
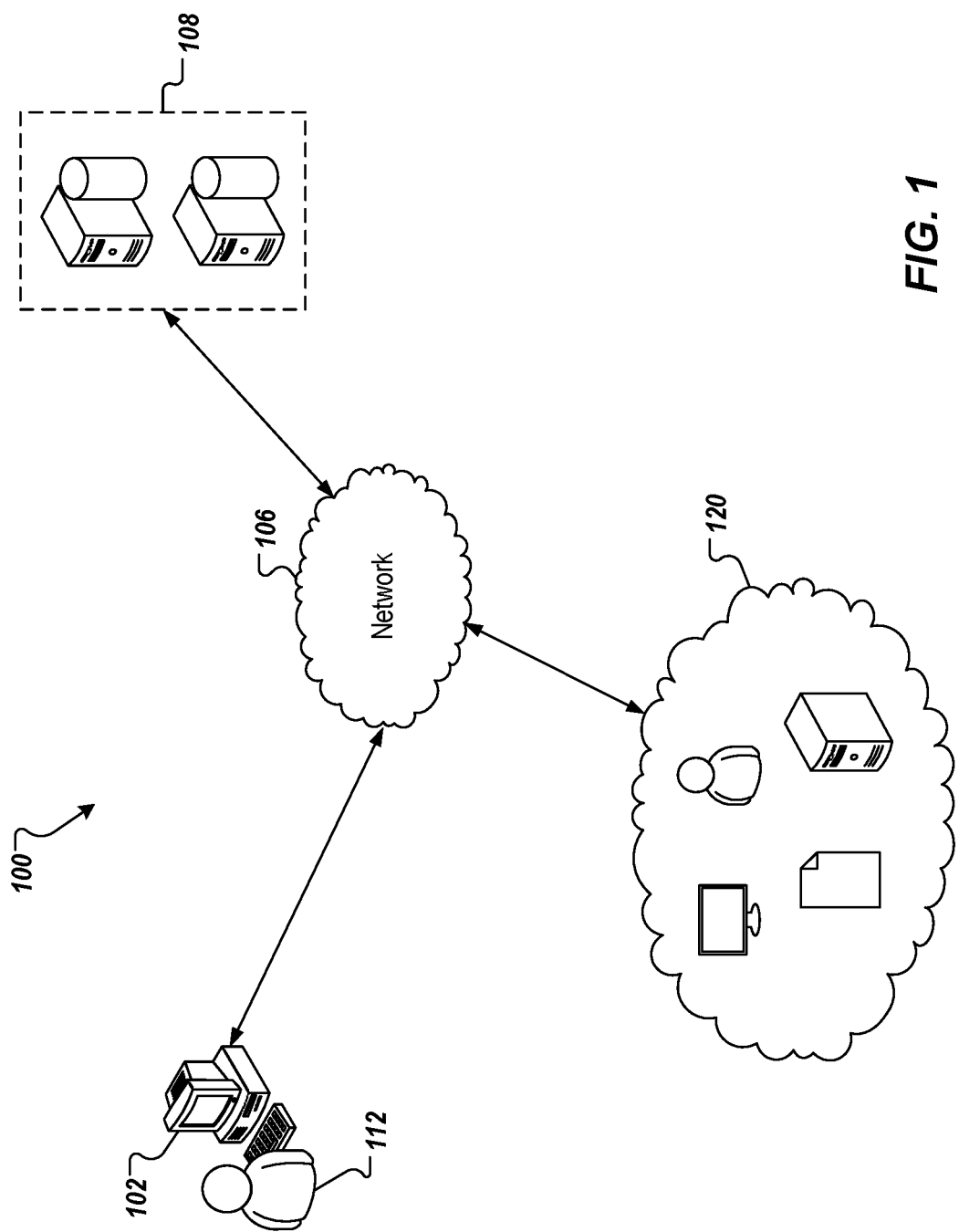
FIG. 1 depicts an example architecture that can be used to execute implementations of the present disclosure.

Implementations of the present disclosure are directed to a duplicate case recommendation engine (DCRE) to identify duplicate cases of adverse effects reported in pharmacovigilance (PV). More particularly, implementations of the present disclosure are directed to a DCRE that identifies duplicate cases present in PV safety reporting by extracting relevant information from a potential new case, conducting a search of existing cases based on the relevant information, and providing a recommendation, if any, of one or more existing cases as potential matches to the new case based on historical data using machine-learning (ML). As described in further detail herein, the DCRE of the present disclosure learns from historical data, applies one or more models to analyze and predict existing cases as closest possible matches to the new case, ranks the identified matches, and for each match, recommends the probability of the match.

In some implementations, actions include receiving, by a duplicate case recommendation engine (DCRE), a document including data representative of an adverse event, providing, by the DCRE, a case including a set of fields, each field of one or more fields in the set of fields being populated with a value, querying, by the DCRE, a safety system based on a query, the query including one or more values of the case, receiving a sparse matrix based on a set of query results provided from the safety system in response to the query, the sparse matrix including two or more vectors, each vector of the two or more vectors representing a historical case score within the safety system, for each historical case, determining, by the DCRE, a score based on a respective vector of the two or more vectors and an input vector representative of the case, each score representing a degree of duplicity between the case and a respective historical case, and providing, by the DCRE, a list of historical cases for display to a user, the list of historical cases including the two or more historical cases in rank order based on respective scores.

To provide context for implementations of the present disclosure, and as introduced above, adverse event reporting can be described as a process of acquisition, triage, data entering, assessment, distribution, reporting, and documenting a case. In some instances, an adverse event can be reported from multiple sources. In the field of healthcare, for example, adverse events, referred to as adverse drug reactions (ADRs), can be reported from healthcare professionals, patients, enterprises-driven patient support programs, clinical trials or post marketing studies, study or research by private/public institutions or individuals, and/or on digital platforms (e.g., social media). Case information captured in these sources is generally provided as free-form text.

In the domain of pharmaceuticals, pharmacovigilance (PV), also known as drug safety, is defined as the pharmacological science relating to the collection, detection, assessment, monitoring, and prevention of adverse effects (also referred to as adverse events) with pharmaceutical products. PV enables pharmaceutical companies and regulatory authorities to assess benefits and risks of drugs throughout the life-cycle of a drug and potentially detect serious adverse events. PV is conducted based on medical information provided from multiple sources (e.g., patients, healthcare providers, medical literature, physicians, a sales team of a pharmaceutical company, pharmacists). Information collected from different sources needs to be processed in a defined consistent way for electronic submission to the regulatory authorities (e.g., Food and Drug Administration (FDA), World Health Organization (WHO), Medicines and Health Regulatory Agency (MHRA), European Medicines Agency (EMA).

Example PV systems are described in further detail in commonly assigned U.S. 2016/0048655 and U.S. 2019/0005019, the disclosures of which are expressly incorporated herein by reference in their entireties.

Enterprises, such as pharmaceutical companies, need to address adverse events to, among other reasons, to serve public health, foster a sense of trust with customers (patients), and proactively monitor effects to prevent product withdrawal from market due to safety issues. However, in many instances, multiple reports of the same adverse effects occur. Consequently, an enterprise may require large back offices in order process large volumes of electronic documents that record reports of adverse effects. Processing of the large volumes of electronic documents can include manual review of the electronic documents and extracting relevant information pertaining to an adverse effect from the document. In some reporting systems, collated data is manually entered. Because information is received from multiple, disparate sources and different users using data entry programs to input data, it often occurs that duplicate reports of an adverse effect are registered in the reporting system.

In order to maintain high quality data, duplicate identification of reports of adverse effects is required, such that documents that are follow-ups to an adverse effect that has already been reported can be managed in an appropriate manner. Traditionally, reporting systems implement manual identification of duplicate reporting using, for example, a drill-down technique using a computer-implemented search system (e.g., iterative submission of search queries). More particularly, a user (also referred to as a case processor) manually enters field combinations into a computer-implemented search tool that are used to search electronic documents, and, in response, the reporting system fires an exact match query. The user reviews the electronic documents returned in response to the query. Accordingly, traditional resources are both time- and resource-inefficient. That is, for example, repeated, iterative searching and review of electronic documents consumes computing resources (e.g., processors, memory).

In view of the above context, implementations of the present disclosure are directed to a duplicate case recommendation engine (DCRE) to identify duplicate cases of adverse effects reported in PV. As described in further detail herein, the DCRE of the present disclosure enables time- and resource-efficient identification and handling of duplicate cases in the PV domain. For example, implementations of the present disclosure obviate the need for iterative searches to be conducted. In this manner, expenditure of technical resources for each iteration of search is avoided. Further, by identifying duplicate cases, redundant electronic documents can be identified and one or more copies can be deleted, thereby reducing the memory consumed in storing such documents.

FIG. 1 depicts an example architecture 100 in accordance with implementations of the present disclosure. In the depicted example, the example architecture 100 includes a client device 102, a network 106, and a server system 108. The server system 108 includes one or more server devices and databases (e.g., processors, memory). In the depicted example, a user 112 interacts with the client device 102.

In some examples, the client device 102 can communicate with the server system 108 over the network 106. In some examples, the client device 102 includes any appropriate type of computing device such as a desktop computer, a laptop computer, a handheld computer, a tablet computer, a personal digital assistant (PDA), a cellular telephone, a network appliance, a camera, a smart phone, an enhanced general packet radio service (EGPRS) mobile phone, a media player, a navigation device, an email device, a game console, or an appropriate combination of any two or more of these devices or other data processing devices. In some implementations, the network 106 can include a large computer network, such as a local area network (LAN), a wide area network (WAN), the Internet, a cellular network, a telephone network (e.g., PSTN) or an appropriate combination thereof connecting any number of communication devices, mobile computing devices, fixed computing devices and server systems.

In some implementations, the server system 108 includes at least one server and at least one data store. In the example of FIG. 1, the server system 108 is intended to represent various forms of servers including, but not limited to a web server, an application server, a proxy server, a network server, and/or a server pool. In general, server systems accept requests for application services and provides such services to any number of client devices (e.g., the client device 102 over the network 106). In accordance with implementations of the present disclosure, and as noted above, the server system 108 can host an agile security platform.

In some implementations, the DCRE of the present disclosure is hosted by the server system 108. In some examples, the DCRE is part of a PV platform hosted by the server system 108. In some examples, the PV platform can be used to manage cases related to adverse effects of pharmaceutical products. For example, the PV platform is used for the collection, detection, assessment, and monitoring of adverse effects to define cases that can be used to prevent future occurrences of adverse effects. For example, one or more data sources 120 can be the source of reporting of an adverse effect associated with one or more pharmaceuticals. Examples of the data sources 120 can include, without limitation, health care professionals, patients, enterprises-driven patient support programs, clinical trials, post marketing studies, studies or research by private/public institutions or individuals, and/or on digital platforms (e.g., social media). As described in further detail herein, the DCRE of the present disclosure enables identification of duplicate cases to conserve resources within the PV process and provide high-quality data for each incident of an adverse effect. In some examples, the user 112 submits information (e.g., manually, upload of document), which is processed by the DCRE to determine whether the information is representative of an already existing case (e.g., the same occurrence of adverse effects has been reported again).

Figure 2:
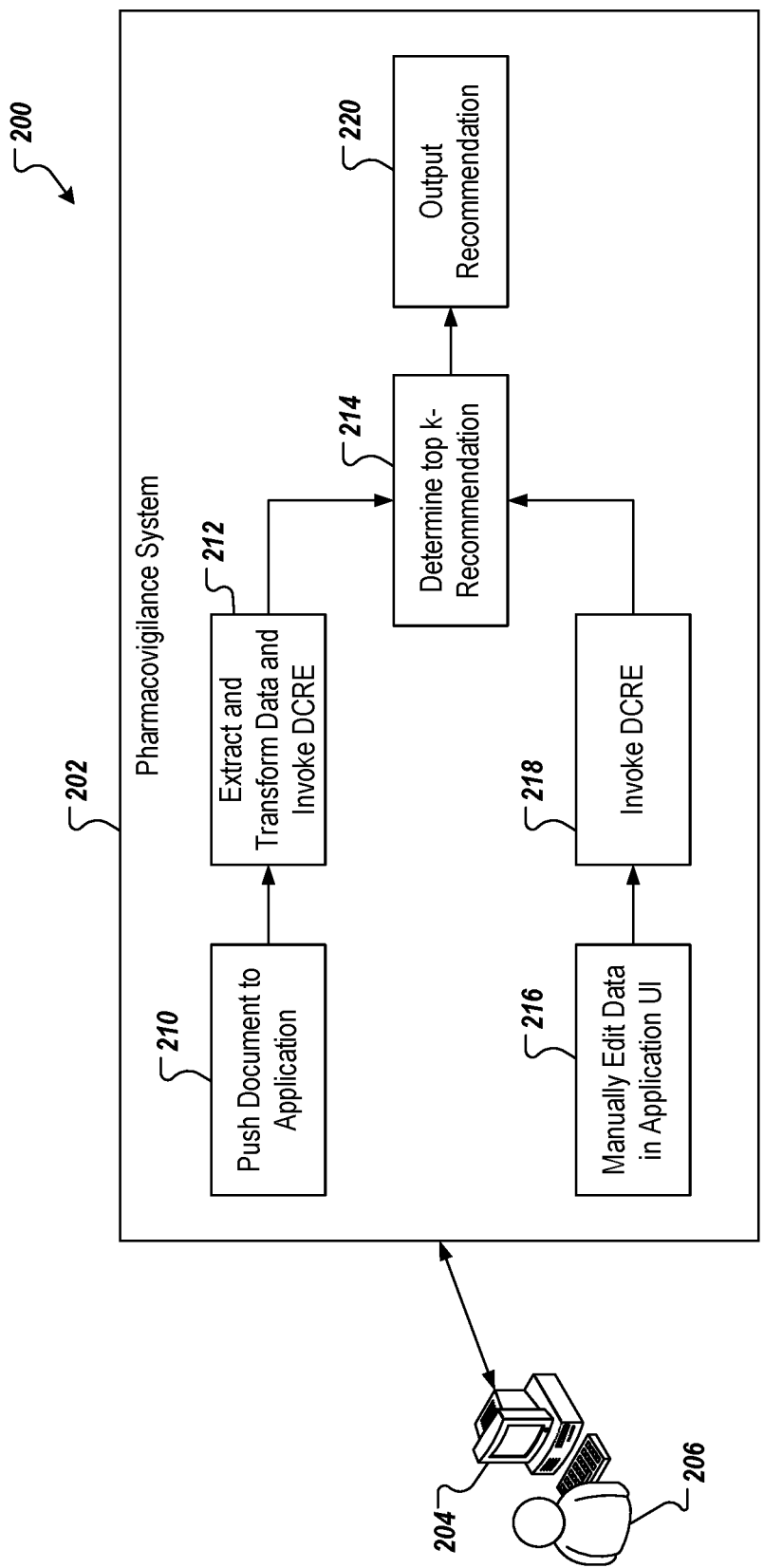
FIG. 2 depicts an example workflow in accordance with implementations of the present disclosure.

FIG. 2 depicts an example workflow 200 in accordance with implementations of the present disclosure. FIG. 2 includes a PV system 202 and a computing device 204 that is used by a user 206. In some implementations, and as described in further detail herein, the PV system 202 operates in one of a first mode and a second mode to provide one or more recommendations, each recommendation being a historical case that a current case may be duplicative of. In some examples, in the first mode, the PV system 202 processes one or more documents representative of a current case that includes occurrence of an adverse effect associated with one or more drugs. In some examples, in the second mode, the PV system 202 processes data that has been modified and that is based on one or more documents representative of the current case, which were previously processed.

In some examples, the user 206 submits one or more documents, each provided as a computer-readable file, to the PV system 202 using the computing device 204. In some examples, a document is representative of a current case and includes data representative of an adverse effect associated with one or more drugs. In some examples, documents can be provided from one or more sources (e.g., healthcare professionals, patients, enterprises-driven patient support programs, clinical trials or post marketing studies, study or research by private/public institutions or individuals, and/or on digital platforms). Example documents can include, without limitation, documents published by The Council for International Organizations of Medical Sciences (CIOMS), reporting forms (e.g., Medwatch published by the U.S. Department of Health and Human Services), documents published through Patient Support Programs (PSP), documents published through Market Research Programs (MRP), custom forms, literature, and the like.

In the example of FIG. 2, the example workflow executed by the PV system 202 includes a first sub-workflow based on the first mode, introduced above, and a second sub-workflow based on the second mode, also introduced above. In some examples, the first sub-workflow includes pushing the document to an application 210, extracting and transforming data from the document and invoking the DCRE 212, determining the top k-recommended historical cases 214 and outputting a recommendation 220. In some examples, the second sub-workflow includes manually editing data through an application UI 216, invoking the DCRE 218, determining the top k-recommended historical cases 214 and outputting a recommendation 220. Each of the operations depicted in the example workflow, including the first sub-workflow and the second sub-workflow are described in further detail herein.

Figure 3:
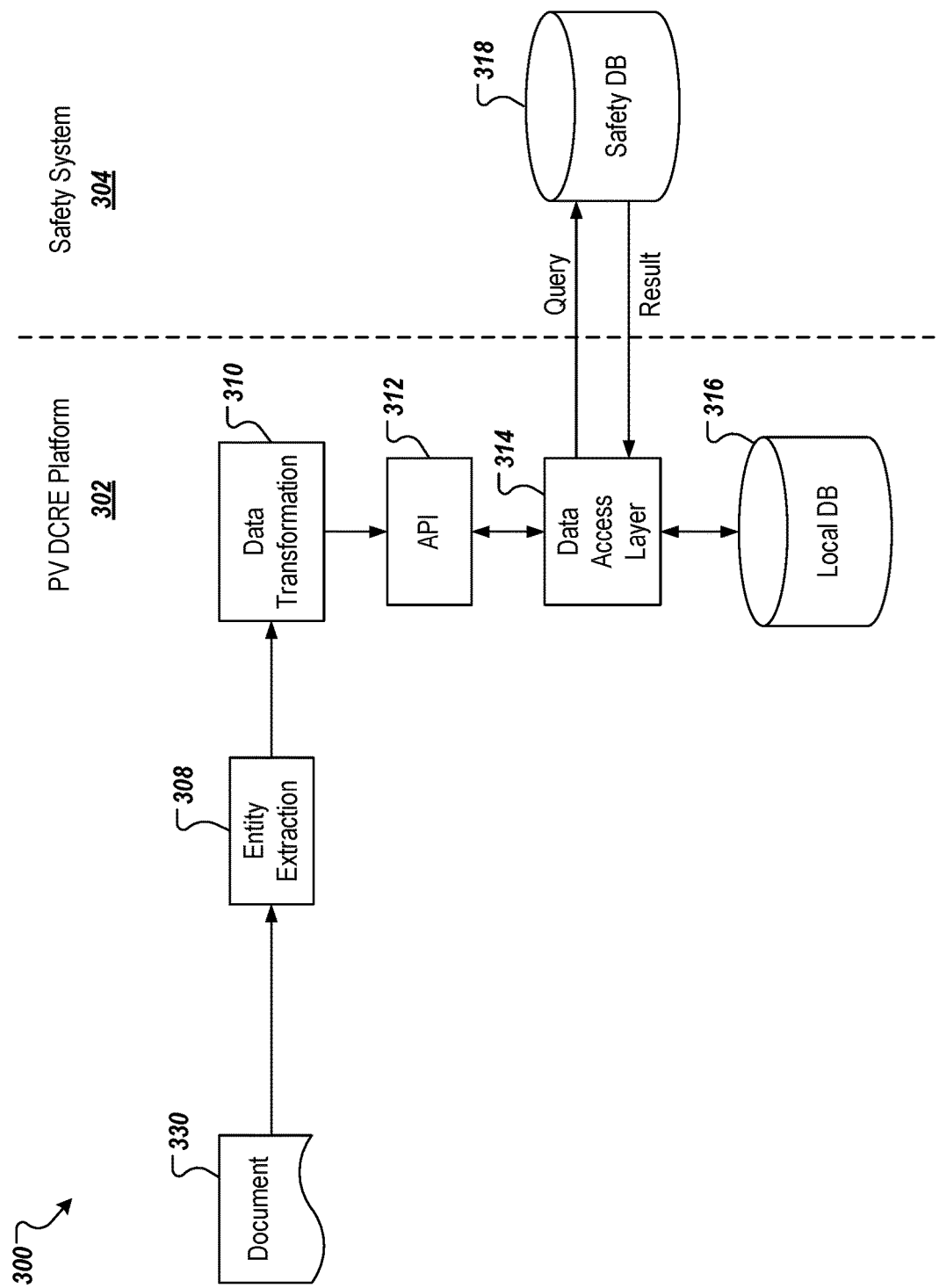
FIG. 3 depicts an example conceptual architecture in accordance with implementations of the present disclosure.

FIG. 3 depicts an example conceptual architecture 300 in accordance with implementations of the present disclosure. The example conceptual architecture 300 includes a PV DCRE platform 302 and a safety system 304. In the depicted example, the PV DCRE platform 302 includes an entity extraction module 308, a data transformation module 310, an application programming interface (API) 312, a data access layer 314, and a local database 316. In the depicted example, the safety system 304 includes a safety database 318.

In accordance with implementations of the present disclosure, and as described in detail herein, the PV DCRE platform 302 receives a document 330 (e.g., provided as a computer-readable document) that represents reporting of an adverse event (e.g., adverse reaction to a drug). The PV DCRE platform 302 processes the document 330 to generate a query that is used to query the safety system 304, which provides a query result. In some implementations, the query at least partially includes a vector that is representative of data provided in the document 330. In some implementations, the query result is provided as a table of one or more result vectors, each result vector representing a historical case that is a potential match to the adverse event reported in the document 330. In some implementations, the PV DCRE platform 302 processes the query result to provide a ranked list of candidate matches, each candidate match representing a potential match between the adverse event reported in the document 330 and a historical case.

In some examples, the document 330 can record an adverse event as a spontaneous event, literature, or clinical trial. A spontaneous adverse event can include a patient reporting an adverse event to a healthcare professional (e.g., doctor, nurse) and the document 330 can be generated based on recording information provided by the patient and/or observed by the healthcare professional. Literature can include, without limitation, published studies and/or papers that discuss one or more adverse events. Clinical trials can include information and results of clinical trials of one or more drugs recorded within the document 330.

In further detail, the entity extraction module 308 receives the document 330 and processes the document 330 using one or more natural language processing (NLP) techniques to recognize one or more named entities represented within the document 330. Example NLP techniques can include, without limitation, language detection and text recognition (e.g., optical character recognition (OCR)), through which the document 330 (e.g., an image, a PDF) is processed to identify instances of text within the document 330. In some examples, instances of text identified within the document 330 is processed using named entity recognition (NER) to identify one or more entities represented within the text. In general, NER is used in information extraction to identify and segment named entities and categorize named entities under one or more predefined classes. Example classes can include, without limitation, person, organization, location, generic name, and brand name. Using NER, entities, such as patient, doctor, hospital, drug, and the like can be identified within the document 330. As described in detail herein, a set of entities (including one or more entities extracted from the document 330) is used to query historical cases of the safety system 304 to identify any potential matches.

In some implementations, the data transformation module 310 receives the set of entities from the entity extraction module 308. In some examples, the data transformation module 310 receives the document 330 and/or data representative of the document 330. In some implementations, the data transformation module 310 extracts medical data information from the received input, composes a document (e.g., Javascript object notation (JSON) document) based on the received input, composes a case based on the received input, and executes data transformation to transform at least a portion of the data recorded in the case.

In some implementations, the data transformation module 310 transforms data included in the case. In some examples, and without limitation, data transformation can be performed on one or more of dates, terms, and drugs. For example, the document 330 can include one or more dates that may be in one or more formats. For example, and without limitation, dates in the document 330 can be provided in YEAR, MONTH-YEAR, DAY-MONTH-YEAR, YEAR-MONTH-DAY, MONTH-DAY-YEAR. In some examples, the data transformation module 310 transforms dates to be provided in an expected format (e.g., MONTH-DAY-YEAR). As one example, if the document 330 includes just a year (e.g., 2019), the data transformation module 310 can provide a date of Jun. 1, 2019. For example, a rule can be provided that any dates provided as only a year, are transformed to include June 1 of that year. As another example, if the document 330 includes a month and a year (e.g., August 2019), the data transformation module 310 can provide a date that include the first day of the month (e.g., Aug. 1, 2019). For example, a rule can be provided that any dates provided as a month and year, are transformed to include the first day of the month. As still another example, if the document 330 includes a date in DAY-MONTH-YEAR or YEAR-MONTH-DAY, the data transformation module 310 can provide the date in MONTH-DAY-YEAR.

In some implementations, data transformation can include transforming low-level terms (LLTs) to one or more upper level terms, such as preferred terms (PTs) and/or high-level terms (HLTs). Example terms and hierarchies are provided in the Medical Dictionary for Regulatory Activities (MedDRA) provided by The International Council for Harmonization of Technical Requirements for Pharmaceuticals for Human Use (ICH). For example, the low-level description "feeling queasy" can be transformed into a PT of "nausea," which can be transformed into a HLT of "nausea and vomiting symptoms." In some implementations, data transformation can include providing drug names, generic drug names, and/or brand names. For example, a drug name (e.g., acetaminophen) that is included in the document 330 can be processed to provide one or more brand names (e.g., Tylenol, Paracetamol).

In some implementations, the case can be represented as a set of fields. The set of fields can include any appropriate number of fields (e.g., 10 fields, 20 fields). In the case of the document 330 representing a spontaneous report, example fields can include, without limitation, ID (e.g., MRF control number), last name of reporter, first name of reporter, country of incidence, generic drug name, product name, date-of-birth (DOB) of patient, gender of patient, and age of patient. In the case of the document 330 representing literature, example fields can include, without limitation, ID (e.g., MRF control number), article title, last name of primary author, first name of primary author, last name(s) of secondary author(s), first name(s) of secondary author(s), country of incidence, generic drug name, product name, date-of-birth (DOB) of patient, gender of patient, and age of patient. In the example case of the document 330 representing a clinical trial, ID (e.g., MRF control number), study identifier, last name of reporter, first name of reporter, country of incidence, generic drug name, product name, date-of-birth(s) (DOB s) of patient(s), gender(s) of patient(s), and age(s) of patient(s).

In some examples, each field either contains a value or is absent a value. For example, if the document 330 is processed and is absent the first name of the reporter (e.g., the person (doctor, nurse, patient)) that reported the adverse event represented in the document 330, the field corresponding to the first name of the reporter is blank. As another example, if the document 330 is processed and includes the last name of the reporter that reported the adverse event represented in the document 330, the field corresponding to the last name of the reporter is populated with the last name of the reporter as provided in the document 330.

The data transformation module 310 submits the case to the data access layer 314 through the API 312. In some examples, the data transformation module 310 submits the case in an API call to the API 312. In some examples, the API call has a payload that includes the case (e.g., data describing the case including one or more of the extracted entities). In some implementations, the data access layer 314 processes the API call to generate a query that is used to query the safety system 304. The data access layer 314 receives the query result from the safety system 304.

In some implementations, and as described in further detail herein, querying of the safety system 304 is performed based on a set of search query parameters, and query results are processed based on an input vector and a field weight vector. In some examples, the search query parameters include values that are provided for in the case, and are used to provide one or more queries (e.g., SQL queries) to generate search results. In some examples, the input vector is an array of zeroes (0's) and/or ones (1's) that is determined based on the presence or absence of values in fields of the case. Without limitation, the following first example case can be considered:

| Reporter First Name | Reporter Last Name | ... | Pat. Gender | Pat. DOB |
|---|---|---|---|---|
| Barnaby | Jones | ... | F | Jun. 1, 2000 |

In view of the first example case, the following example search query parameters can be provided: [Barnaby, Jones, ..., F, Jun. 1, 2000]. Also, in view of the first example case, the following input vector can be provided: [1, 1, ..., 1, 1]. Without limitation, the following second example case can be considered:

| Reporter First Name | Reporter Last Name | ... | Pat. Gender | Pat. DOB |
|---|---|---|---|---|
|  | Dobson | ... |  | Aug. 8, 1973 |

In view of the second example case, the following example search query parameters can be provided: [Dobson, ..., Aug. 8, 1973]. Also, in view of the second example case, the following input vector can be provided: [0, 1, ..., 0, 1].

In some implementations, the query to the safety system 304 includes the search query parameters. In some examples, the query is used to query a set of tables within the safety system 304. Example tables include, without limitation, an event table (e.g., CASE_EVENT, which records spontaneous events that are reported), a literature table (e.g., CASE_LITERATURE), a master table (e.g., CASE_MASTER), a notes and attachments table (e.g., CASE_NOTES_ATTACH), a patient information table (e.g., CASE_PAT_INFO), a product table (e.g., CASE_PRODUCT), a study table (e.g., CASE_STUDY), and a reporters table (e.g., CASE_REPORTERS). An example query based on the first example case can include:
    SELECT [R_FIRST_NAME],[R_LAST_NAME], ..., [P_GENDER],[P_DOB] FROM [CASE_EVENT] WHERE [R_FIRST_NAME]=BARNABY OR [R_LAST_NAME]=JONES OR ... OR [P_GENDER]=F OR [P_DOB]=06-01-2000

In some examples, multiple queries can be provided, a query for each table.

In some examples, the safety system 304 returns a set of query results that includes one or more historical cases. For example, the set of query results can include historical cases having one or more values that match respective values provided in the query. Without limitation, an example set of query results based on the above example query for the first example case can include:

| Case1 | Barnaby | Jones | ... | F | Jun. 1, 2000 |
|---|---|---|---|---|---|
| Case2 |  | Jones | ... |  |  |
| Case3 | Barnaby |  | ... | F | Jun. 1, 2000 |
| Case4 |  | Jones | ... |  |  |
| ... | ... | ... | ... | ... | ... |
| Case10 |  |  | ... | F |  |

In some implementations, a sparse matrix is provided, which includes a set of vectors, each vector corresponding to a respective historical case in the set of query results. In some examples, each vector in the sparse matrix is an array of zeroes (0's) and/or ones (1's) that is determined based on the presence or absence of values in fields of the respective historical case. Without limitation, an example sparse matrix based on the above example set of query results can include:

| Case1 | 1 | 1 | ... | 1 | 1 |
|---|---|---|---|---|---|
| Case2 | 0 | 1 | ... | 0 | 0 |
| Case3 | 1 | 0 | ... | 1 | 1 |
| Case4 | 0 | 1 | ... | 0 | 0 |
| ... | ... | ... | ... | ... | ... |
| Case10 | 0 | 0 | ... | 1 | 0 |

In accordance with implementations of the present disclosure, the case is compared to each of the historical cases represented in the set of query results by generating a set of scores. In some implementations, the set of scores includes, for each historical case, a field-level score, a similarity score, and a final score. In some examples, and as described in further detail herein, a field level score is determined for each historical case in the set of query results based on a weighted base vector and a respective vector in the sparse matrix. In some examples, and as described in further detail herein, a similarity score is determined for each historical case in the set of query results based on the input vector representative of the case and a respective vector in the sparse matrix. In some examples, and as described in further detail herein, a final score is determined for each historical case in the set of query results based on the respective field-level score and the respective similarity score. In some implementations, historical cases in the set of query results are ranked based on the final scores and are provided as output indicating historical cases that may be duplicative of the case.

Figure 4:
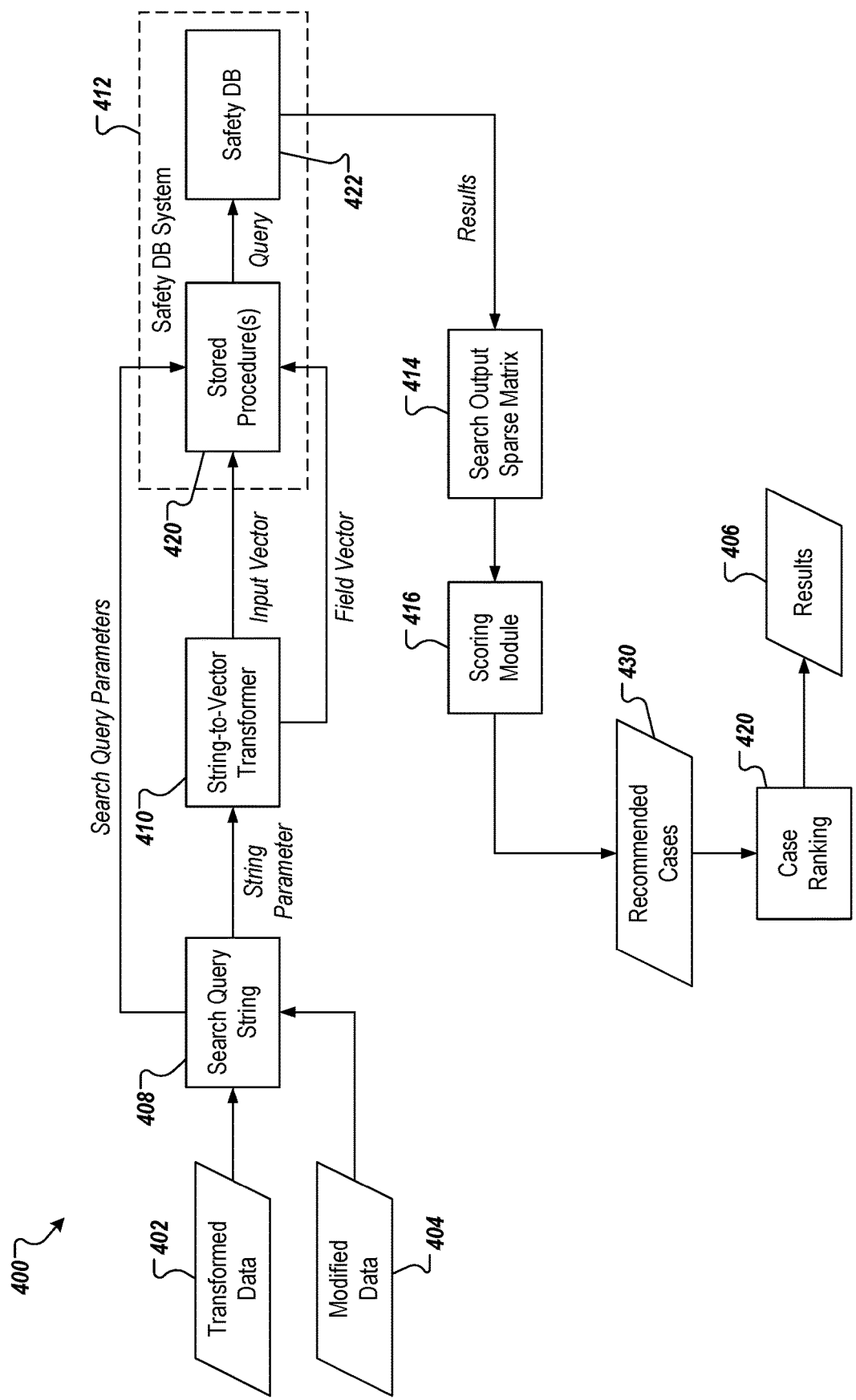
FIG. 4 depicts an example detailed workflow in accordance with implementations of the present disclosure.

FIG. 4 depicts an example detailed workflow 400 in accordance with implementations of the present disclosure. In some implementations, transformed data 402, if operating in the first mode, or modified data 404, if operating in the second mode, is processed through the example workflow 400 to provide results 406. The example of FIG. 4 includes a search query string module 408, a string-to-vector transformer module 410, a safety system 412, a search output sparse matrix module 414, a scoring module 416, and a case ranking module 420. The safety system 412 includes a stored procedures module 420 and a safety database 422. In some examples, the stored procedures module 420 provides a query that is used to search the safety database 422. Although the stored procedures module 420 is depicted as part of the safety system 412 in FIG. 4, in some implementations, provision of the query can be performed external to the safety system 412. For example, and as depicted in FIG. 3, the data access layer 314 of the PV DCRE platform 302 provides the query to the safety system 304. For example, the stored procedures 420 can be provided in the PV DCRE platform 302 of FIG. 3.

In some implementations, the search query string module 408 receives the transformed data 402 or the modified data 404 and generates a set of search query parameters and a string parameter. In some examples, the set of search query parameters is provided to the safety system 412 and the string parameter is provided to the string-to-vector transformer module 410. In some implementations, the string-to-vector transformer module 410 receives a field vector that includes an array of weights from an offline weight calculation module (not depicted in FIG. 4). In some examples, the weights provided in the field vector represent a relative significance of a field of a case relative to other fields in the case. In some examples, the relative significance is a measure of the influence a respective field has in identifying one or more historical cases that may be a match to the case, as described in further detail herein.

In some implementations, offline weight calculation includes determining a value for each weight in a respective array of weights. In some examples, each weight for a candidate field is calculated as a probability of the field being present when a case is identified as a duplicate. The following example relationship can be used:

Initial weight=(count of field present)/(Total number of case present)

where the numerator is 1, if the field is present and is 0 if not present when a duplicate case was identified. Here, the initial weight is the calculated probability for the field and the denominator is the total number of samples considered from a population of samples. In some examples, weight consistency is measured across the sample by selecting data across quarter and conducting hypothesis testing using T-Test, for example. Each weight can be subsequently optimized by setting it up as an optimization problem that is solved using linear programming or gradient descent technique. Historical evidence bias will be controlled using exponential smoothing technique to improve the weight optimization.

In some implementations, the string-to-vector transformer module 410 processes the string parameter to provide an input vector. Example input vectors are provided above. An example input vector and an example field vector are described in further detail herein with reference to FIG. 5.

In some implementations, the stored procedures module 420 process the search query parameters, the input vector, and the weighted input vector to provide one or more queries that are used to query the safety database 422. An example query is provided above. In some implementations, the safety system 412 processes the query to provide a set of query results. An example set of query results is provided above. In some examples, the set of query results are output to the search output sparse matrix module 414. In the example of FIG. 4, the search output sparse matrix module 414 is depicted as external to the safety system 412. In some examples, the search output sparse matrix module 414 is depicted as external to the safety system 412. The search output sparse matrix module 414 provides a sparse matrix by converting each representation of a historical case to a vector. An example sparse matrix is provided above.

In some implementations, the scoring module 416 generates a set of scores for each historical case in the set of query results. As introduced above, the set of scores includes, for each historical case, a field-level score, a similarity score, and a final score, described in further detail herein. In some examples, the scoring module 416 outputs a set of recommended cases 430. In some examples, the set of recommended cases includes two or more cases and, for each case, a final score.

In some implementations, a field level score is determined for each historical case in the set of query results based on a weighted base vector and a respective vector in the sparse matrix. In some examples, the weighted base vector is determined based on the input vector representative of the case and the field vector, which includes weights for respective fields, as described herein. In some examples, the weighted base vector is calculated as the product of the input vector and the field vector. The weighted base vector represents a relative importance of respective fields of the case in comparing the case to historical cases provided in the set of query results. An example weighted base vector is described herein with reference to FIG. 5.

In some implementations, the field-level score is determined by multiplying the weighted base vector by the vector for a case to provide field weights for the case, and the field weights are used to calculate the field-level score. The following example relationship can be considered:

Field Importance=Resultant Matrix*({Input Vector}pointwise multiplication{weight vector})$^T$ In some examples, the calculated value is normalized based on the following example relationship:

Normalized Outcome=Field Importance/Σ({Input Vector}pointwise multiplication{weight vector})

In some implementations, a similarity score is determined for each historical case in the set of query results based on the input vector representative of the case and a respective vector in the sparse matrix. In some examples, each similarity score is provided as a cosine similarity score that is calculated between the input vector and a respective vector in the sparse matrix. In some examples, the similarity score is provided within a range (e.g., [0, 1]). In general, cosine similarity between vectors can be described as a measure of similarity between two non-zero vectors (e.g., both vectors have at least one field that is populated with one (1)) of an inner product space that measures the cosine of the angle between the vectors. Two vectors with the same orientation (i.e., are identical) have a cosine similarity of 1, while two vectors that are dissimilar to each other have a cosine similarity of less than 1. In accordance with implementations of the present disclosure, the input vector includes at least one field populated with one (1) and each of the vectors provided in the sparse matrix includes at least one field populated with one (1).

In some implementations, a final score is determined for each historical case in the set of query results based on the respective field-level score and the respective similarity score. In some examples, a final score is calculated based on a combination of the respective field-level score and the respective similarity score. For example, and without limitation, the final score can be calculated as a weighted average of the respective field-level score and the respective similarity score. In some examples, the final score is calculated as a harmonic mean of the respective field-level score and the respective similarity score. An example relationship for calculating the final score can be provided as:

$$\frac{1}{\alpha \frac{1}{FV} + (1-\alpha)\frac{1}{S}}$$

where FV is the field-level score, S is the similarity score, and α is a tuning parameter.

In some implementations, historical cases in the set of query results are ranked based on the final scores and are provided as output indicating historical cases that may be duplicative of the case. More particularly, the case ranking module 420 receives the set of recommended cases 430, and ranks the cases based on the respective final scores. In some examples, cases having a greater final score are ranked higher than cases having a lower final score. The ranked cases are provided as the results 406.

In some implementations, the results 406 are displayed to a user that submitted the case for processing (e.g., the case, from which the transformed data 402 was provided). In some examples, the user can accept the results 406 (e.g., if the results 406 indicate an exact match where a historical case includes a final score equal to 1). In some examples, the user can modify the transformed data 402 to provide the modified data 404 then re-run the duplicate search (e.g., the second mode). For example, the user can add a value to, edit a value of, and/or delete a value from the transformed data 402 to provide the modified data 404. The duplicate search can be re-run, as described herein, based on the modified data 404 to again provide results 406.

FIG. 5 depicts an example duplicate search in accordance with implementations of the present disclosure. In the example of FIG. 5, a field vector 500, an input vector 502, a weighted base vector 504, a sparse matrix 506, and a set of recommended cases 508.

As described herein, the field vector 500 includes an array of weights, each weight corresponding to a respective field and representative of a relative influence of the respective field in identifying duplicate cases. In the example of FIG. 5, the field vector 500 (which, as depicted, only represents the first 8 fields of a case) indicates that field 1 and field 2 are of the same relative importance (e.g., both are populated with weights of 0.34), while field 8 is of the highest importance and field 4 is of the lowest importance of the fields depicted.

The input vector 502 includes an array of values that are representative of the case, for which a duplicate search is to be conducted. As described herein, the input vector 502 is an array of zeroes (0's) and/or ones (1's) that is determined based on the presence or absence of values in fields of the case. In the example of FIG. 5, at least fields 1 to 8 of the case are populated with values. Consequently, fields 1 to 8 of the input vector are each populated with one (1).

The weighted base vector 504 is calculated as a product of the field vector 500 and the input vector 502. As described herein, the weighted base vector 504 is used to calculate the field-level score for each of the historical cases represented in the sparse matrix 506. That is, for example, the weighted base vector 504 is multiplied by the vector of a respective case to provide a field-weighted vector, and the field level score is determined for the respective case based on the field-weighted vector.

As also described herein, historical cases in the set of recommended cases 508 can be ranked (e.g., by the case ranking module 420) to provide results (e.g., the results 406) that include recommended historical cases in rank order. In the example of FIG. 5, case1 is determined to be identical to the case that was submitted for duplicate search (e.g., the case represented by the input vector 502). Consequently, it can be determined that the case is a duplicate of a case that had been previously received and is already recorded in the safety system.

Figure 6:
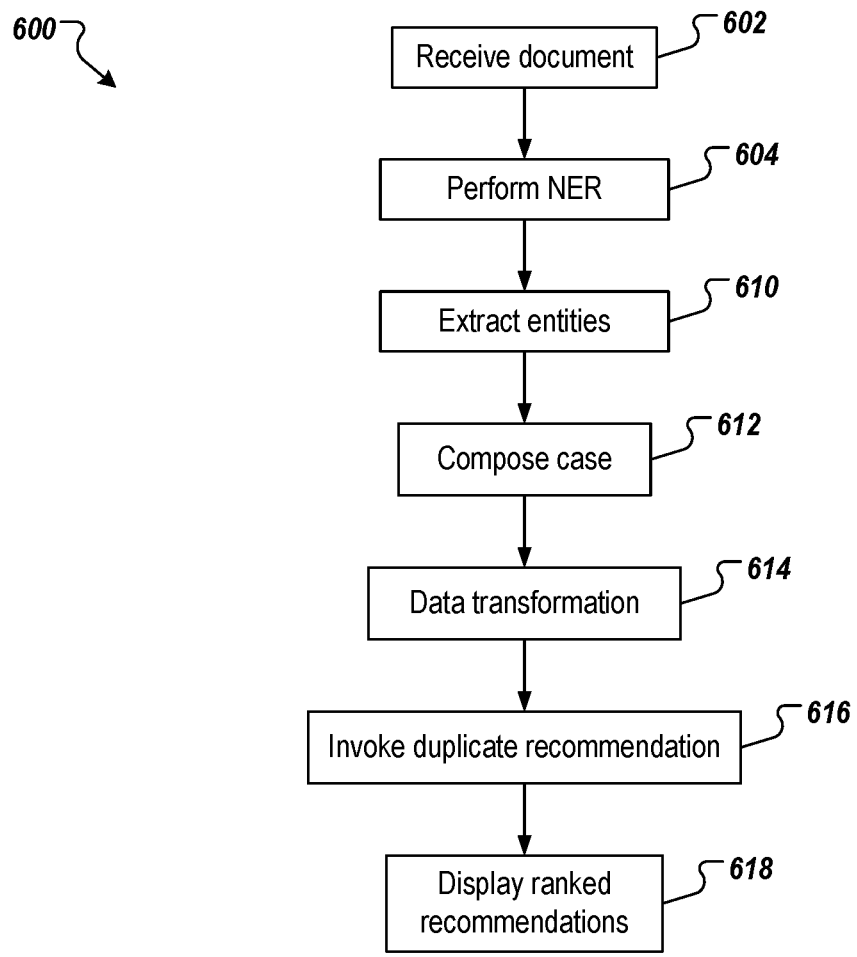
FIG. 6 depicts an example process that can be executed in accordance with implementations of the present disclosure.

FIG. 6 depicts an example process 600 that can be executed in accordance with implementations of the present disclosure. In some implementations, the example process 600 may be performed using one or more computer-executable programs executed using one or more computing devices.

A document is received (600). For example, and as described in detail herein, the PV DCRE platform 302 receives a document 330 (e.g., provided as a computer-readable document) that represents reporting of an adverse event (e.g., adverse reaction to a drug). In some examples, the document 330 records data as part of a spontaneous event, literature, or a clinical trial. NER is performed (604) and one or more entities are extracted (606). For example, and as described herein, the entity extraction module 308 receives the document 330 and processes the document 330 using one or more NLP techniques to recognize one or more named entities represented within the document 330. In some examples, instances of text identified within the document 330 are processed using NER to identify and segment named entities and categorize named entities under one or more predefined classes.

A case is composed (612) and data transformation is performed (614). For example, and as described herein, the data transformation module 310 receives the set of entities from the entity extraction module 308. In some examples, the data transformation module 310 receives the document 330 and/or data representative of the document 330. In some implementations, the data transformation module 310 extracts medical data information from the received input, composes a document (e.g., Javascript object notation (JSON) document) based on the received input, composes a case based on the received input, and executes data transformation to transform at least a portion of the data recorded in the case. In some implementations, the case can be represented as a set of fields (e.g., an array of fields), where each field either contains a value or is absent a value.

Duplicate recommendation is invoked (616). For example, the case is submitted to the data access layer 314 through the API 312. In some implementations, and as described herein, the case is processed (e.g., by the data access layer 314) to generate a query that is used to query the safety system 304. The data access layer 314 receives the query result from the safety system 304. In some implementations, and as described in further detail herein, querying of the safety system 304 is performed based on a set of search query parameters, and query results are processed based on an input vector and a field vector. In some examples, the search query parameters include values that are provided for in the case, and are used to provide one or more queries (e.g., SQL queries) to generate search results. In some implementations, the query to the safety system 304 includes the search query parameters. In some examples, the query is used to query a set of tables within the safety system 304.

In some examples, the safety system 304 returns a set of query results that includes one or more historical cases. For example, the set of query results can include historical cases having one or more values that match respective values provided in the query. In some implementations, a sparse matrix is provided, which includes a set of vectors, each vector corresponding to a respective historical case in the set of query results. In some examples, each vector in the sparse matrix is an array of zeroes (0's) and/or ones (1's) that is determined based on the presence or absence of values in fields of the respective historical case.

In accordance with implementations of the present disclosure, the case is compared to each of the historical cases represented in the set of query results by generating a set of scores. In some implementations, the set of scores includes, for each historical case, a field-level score, a similarity score, and a final score. In some examples, and as described in further detail herein, a field level score is determined for each historical case in the set of query results based on a weighted base vector and a respective vector in the sparse matrix. In some examples, and as described in further detail herein, a similarity score is determined for each historical case in the set of query results based on the input vector representative of the case and a respective vector in the sparse matrix. In some examples, and as described in further detail herein, a final score is determined for each historical case in the set of query results based on the respective field-level score and the respective similarity score. In some implementations, historical cases in the set of query results are ranked based on the final scores and are displayed (618) as output indicating historical cases that may be duplicative of the case.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products, i.e., one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question (e.g., code) that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry (e.g., an FPGA (field programmable gate array) or an ASIC (application specific integrated circuit)).

Processors suitable for the execution of a computer program include, by way of example, both general and special purpose microprocessors, and any one or more processors of any appropriate kind of digital computer. Generally, a processor will receive instructions and data from a read only memory or a random access memory or both. Elements of a computer can include a processor for performing instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks). However, a computer need not have such devices. Moreover, a computer may be embedded in another device (e.g., a mobile telephone, a personal digital assistant (PDA), a mobile audio player, a Global Positioning System (GPS) receiver). Computer readable media suitable for storing computer program instructions and data include all forms of non-volatile memory, media and memory devices, including by way of example semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, implementations may be realized on a computer having a display device (e.g., a CRT (cathode ray tube), LCD (liquid crystal display), LED (light-emitting diode) monitor, for displaying information to the user and a keyboard and a pointing device (e.g., a mouse or a trackball), by which the user may provide input to the computer. Other kinds of devices may be used to provide for interaction with a user as well; for example, feedback provided to the user may be any appropriate form of sensory feedback (e.g., visual feedback, auditory feedback, or tactile feedback); and input from the user may be received in any appropriate form, including acoustic, speech, or tactile input.

Implementations may be realized in a computing system that includes a back end component (e.g., as a data server), or that includes a middleware component (e.g., an application server), or that includes a front end component (e.g., a client computer having a graphical user interface or a Web browser through which a user may interact with an implementation), or any appropriate combination of one or more such back end, middleware, or front end components. The components of the system may be interconnected by any appropriate form or medium of digital data communication (e.g., a communication network). Examples of communication networks include a local area network ("LAN") and a wide area network ("WAN") (e.g., the Internet).

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A computer-implemented method for resource-efficient processing of data in pharmacovigilance systems to determine redundancy of a case, the method being executed by one or more processors and comprising:
   receiving, by a duplicate case recommendation engine (DCRE), a document comprising data representative of an adverse event;
   providing, by the DCRE, a case comprising a set of fields, each field of one or more fields in the set of fields being populated with a value;
   querying, by the DCRE, a safety system based on a query, the query comprising one or more values of the case;
   receiving a sparse matrix based on a set of query results provided from the safety system in response to the query, the sparse matrix comprising two or more vectors, each vector of the two or more vectors representing a historical case score within the safety system;
   for each historical case, determining, by the DCRE, a score based on a respective vector of the two or more vectors and an input vector representative of the case, each score representing a degree of duplicity between the case and a respective historical case; and
   providing, by the DCRE, a list of historical cases for display to a user, the list of historical cases comprising the two or more historical cases in rank order based on respective scores.

2. The method of claim 1, wherein each score is determined based on a field-level score and a similarity score of a respective historical case.

3. The method of claim 2, wherein the field-level score is determined based on the input vector and a field vector, the field vector comprising two or more weights, each weight associated with a respective field.

4. The method of claim 3, wherein each of the two or more weights is updated based on the set of query results provided from the safety system.

5. The method of claim 2, wherein the similarity score is calculated as a cosine similarity between the input vector and a respective vector of the two or more vectors.

6. The method of claim 1, further comprising:
   identifying a data value from the document;
   transforming the data value to provide a transformed data value; and
   providing the transformed value as the value populating a field in the set of fields.

7. The method of claim 6, wherein transforming the data value comprises one of changing a format of the data value, adding data to the data value, and generating new data from the data value, the transformed value comprising the new data.

8. The method of claim 7, wherein adding data to the data value comprises adding one or more of a month and a day to the data value.

9. The method of claim 7, wherein generating new data from the data value comprises determining one of a preferred term and a high-level term from the data value, the new data comprising the one of the preferred term and the high-level term.

10. The method of claim 1, further comprising:
    receiving, by the DCRE, user input comprising a modification to the case to provide a modified case;
    querying, by the DCRE, the safety system based on a modified query, the modified query comprising at least one modified value of the modified case;
    receiving a second sparse matrix based on a second set of query results provided from the safety system in response to the modified query; and
    providing, by the DCRE, a second list of historical cases for display to the user, the second list of historical cases comprising two or more historical cases in rank order based on the second sparse matrix.

11. The method of claim 1, wherein the adverse event comprises an adverse drug reaction.

12. A non-transitory computer-readable storage medium coupled to one or more processors and having instructions stored thereon which, when executed by the one or more processors, cause the one or more processors to perform operations for resource-efficient processing of data in pharmacovigilance systems to determine redundancy of a case, the operations comprising:
    receiving, by a duplicate case recommendation engine (DCRE), a document comprising data representative of an adverse event;
    providing, by the DCRE, a case comprising a set of fields, each field of one or more fields in the set of fields being populated with a value;
    querying, by the DCRE, a safety system based on a query, the query comprising one or more values of the case;
    receiving a sparse matrix based on a set of query results provided from the safety system in response to the query, the sparse matrix comprising two or more vectors, each vector of the two or more vectors representing a historical case score within the safety system;

for each historical case, determining, by the DCRE, a score based on a respective vector of the two or more vectors and an input vector representative of the case, each score representing a degree of duplicity between the case and a respective historical case; and providing, by the DCRE, a list of historical cases for display to a user, the list of historical cases comprising the two or more historical cases in rank order based on respective scores.

13. The computer-readable storage medium of claim 12, wherein each score is determined based on a field-level score and a similarity score of a respective historical case.

14. The computer-readable storage medium of claim 13, wherein the field-level score is determined based on the input vector and a field vector, the field vector comprising two or more weights, each weight associated with a respective field.

15. The computer-readable storage medium of claim 14, wherein each of the two or more weights is updated based on the set of query results provided from the safety system.

16. The computer-readable storage medium of claim 13, wherein the similarity score is calculated as a cosine similarity between the input vector and a respective vector of the two or more vectors.

17. The computer-readable storage medium of claim 12, wherein operations further comprise:
identifying a data value from the document;
transforming the data value to provide a transformed data value; and
providing the transformed value as the value populating a field in the set of fields.

18. The computer-readable storage medium of claim 17, wherein transforming the data value comprises one of changing a format of the data value, adding data to the data value, and generating new data from the data value, the transformed value comprising the new data.

19. The computer-readable storage medium of claim 18, wherein adding data to the data value comprises adding one or more of a month and a day to the data value.

20. The computer-readable storage medium of claim 18, wherein generating new data from the data value comprises determining one of a preferred term and a high-level term from the data value, the new data comprising the one of the preferred term and the high-level term.

21. The computer-readable storage medium of claim 12, wherein operations further comprise:
receiving, by the DCRE, user input comprising a modification to the case to provide a modified case;
querying, by the DCRE, the safety system based on a modified query, the modified query comprising at least one modified value of the modified case;
receiving a second sparse matrix based on a second set of query results provided from the safety system in response to the modified query; and
providing, by the DCRE, a second list of historical cases for display to the user, the second list of historical cases comprising two or more historical cases in rank order based on the second sparse matrix.

22. The computer-readable storage medium of claim 12, wherein the adverse event comprises an adverse drug reaction.

23. A system, comprising:
one or more computers; and
a computer-readable storage device coupled to the computing device and having instructions stored thereon which, when executed by the computing device, cause the computing device to perform operations for resource-efficient processing of data in pharmacovigilance systems to determine redundancy of a case, the operations comprising:
receiving, by a duplicate case recommendation engine (DCRE), a document comprising data representative of an adverse event;
providing, by the DCRE, a case comprising a set of fields, each field of one or more fields in the set of fields being populated with a value;
querying, by the DCRE, a safety system based on a query, the query comprising one or more values of the case;
receiving a sparse matrix based on a set of query results provided from the safety system in response to the query, the sparse matrix comprising two or more vectors, each vector of the two or more vectors representing a historical case score within the safety system;
for each historical case, determining, by the DCRE, a score based on a respective vector of the two or more vectors and an input vector representative of the case, each score representing a degree of duplicity between the case and a respective historical case; and
providing, by the DCRE, a list of historical cases for display to a user, the list of historical cases comprising the two or more historical cases in rank order based on respective scores.

24. The system of claim 23, wherein each score is determined based on a field-level score and a similarity score of a respective historical case.

25. The system of claim 24, wherein the field-level score is determined based on the input vector and a field vector, the field vector comprising two or more weights, each weight associated with a respective field.

26. The system of claim 25, wherein each of the two or more weights is updated based on the set of query results provided from the safety system.

27. The system of claim 24, wherein the similarity score is calculated as a cosine similarity between the input vector and a respective vector of the two or more vectors.

28. The system of claim 23, wherein operations further comprise:
identifying a data value from the document;
transforming the data value to provide a transformed data value; and
providing the transformed value as the value populating a field in the set of fields.

29. The system of claim 28, wherein transforming the data value comprises one of changing a format of the data value, adding data to the data value, and generating new data from the data value, the transformed value comprising the new data.

30. The system of claim 29, wherein adding data to the data value comprises adding one or more of a month and a day to the data value.

31. The system of claim 29, wherein generating new data from the data value comprises determining one of a preferred term and a high-level term from the data value, the new data comprising the one of the preferred term and the high-level term.

32. The system of claim 23, wherein operations further comprise:
receiving, by the DCRE, user input comprising a modification to the case to provide a modified case;
querying, by the DCRE, the safety system based on a modified query, the modified query comprising at least one modified value of the modified case;

receiving a second sparse matrix based on a second set of query results provided from the safety system in response to the modified query; and providing, by the DCRE, a second list of historical cases for display to the user, the second list of historical cases comprising two or more historical cases in rank order based on the second sparse matrix.

33. The system of claim 23, wherein the adverse event comprises an adverse drug reaction.

\* \* \* \* \*